United States Patent [19]

Ansell

[11] Patent Number: 5,713,835
[45] Date of Patent: Feb. 3, 1998

[54] ORTHOPAEDIC MATERIAL

[75] Inventor: Christopher Ansell, Easingwold, United Kingdom

[73] Assignee: Smith & Nephew plc, London, England

[21] Appl. No.: 545,624

[22] PCT Filed: Apr. 29, 1994

[86] PCT No.: PCT/GB94/00920

§ 371 Date: Nov. 3, 1995

§ 102(e) Date: Nov. 3, 1995

[87] PCT Pub. No.: WO94/25076

PCT Pub. Date: Nov. 10, 1994

[30] Foreign Application Priority Data

May 5, 1993 [GB] United Kingdom ............... 9309275

[51] Int. Cl.[6] ........................................... A61F 5/00
[52] U.S. Cl. ....................... 602/2; 602/6; 602/79; 602/3; 428/290
[58] Field of Search ..................... 602/1–3, 5–6, 602/8, 900, 79; 428/290

[56] References Cited

U.S. PATENT DOCUMENTS

| | | | |
|---|---|---|---|
| 3,874,376 | 4/1975 | Dart et al. | 128/90 |
| 4,058,400 | 11/1977 | Crivello | 96/86 |
| 4,307,177 | 12/1981 | Crivello | 430/281 |
| 4,427,003 | 1/1984 | Fennimore et al. | 128/90 |
| 4,499,251 | 2/1985 | Omura et al. | 526/278 |
| 4,537,940 | 8/1985 | Omura et al. | 526/278 |
| 5,354,259 | 10/1994 | Scholz et al. | 602/8 |
| 5,364,693 | 11/1994 | Moren et al. | 428/263 |
| 5,405,643 | 4/1995 | Scholz | 427/2.31 |
| 5,449,550 | 9/1995 | Yasis et al. | 428/254 |
| 5,455,060 | 10/1995 | Neamy et al. | 427/2.31 |

FOREIGN PATENT DOCUMENTS

| | | |
|---|---|---|
| 1 491 540 | 1/1977 | United Kingdom . |
| 1 516 511 | 7/1978 | United Kingdom . |
| 1 518 141 | 7/1978 | United Kingdom . |
| 1518141 | 7/1978 | United Kingdom ............... 96/86 |

OTHER PUBLICATIONS

Richard Lewis, editor, "Hawley's Condensed Chemical Dictionary", 12th edition, citations of polystyrene and styrene, pp. 941 and 1097, 1993.

*Primary Examiner*—Michael Powell Buiz
*Assistant Examiner*—Chalin Smith
*Attorney, Agent, or Firm*—Larson & Taylor

[57] ABSTRACT

An orthopaedic splinting or casting material comprises a substrate which carries a hardenable resin containing a multi-functional vinyl ether monomer, an agent which when mixed with the monomer increases the viscosity thereof and a catalyst capable of causing the resin to harden when exposed to actinic radiation.

16 Claims, No Drawings

ORTHOPAEDIC MATERIAL

The present invention relates to a hardenable material which comprises a substrate which carries a resin containing a multifunctional vinyl ether compound which hardens in the presence of actinic radiation and a catalyst. More specificially, this invention relates to an orthopaedic splint or cast material which comprises a substrate which carries a resin which contains a multifunctional vinyl ether monomer compound and an agent which when mixed with the monomer increases the viscosity thereof and which resin hardens in the presence of a suitable catalyst and actinic radiation to form a strong splint or cast.

Traditionally, Plaster of Pads has been used in orthopaedic bandages or splinting bandages. However, such bandages have many disadvantages including heaviness, absorbing moisture, rapid soiling and X-ray opacity. There have been many attempts to replace Plaster of Paris with a lighter material which did not possess its other disadvantages.

It has now been found that by employing a mixture of a multifunctional vinyl ether monomer, an agent which when mixed with the monomer increases the viscosity thereof and a photoinitiation cationic catalyst to impregnate an orthopaedic bandage substrate, an orthopaedic splinting or casting material can be obtained which does not require the use of fillers and can be simply cured by exposure to radiation to give a satisfactory, hard cast.

The cationic polymerisation of multifunctional vinyl ethers initiated by irradiation has been described in, for example, European Patent Application Nos 94915 and 109851 and U.S. Pat. No. 4,307,177. The curable compositions disclosed therein can be used as molding compounds, adhesives, printing inks and other applications in which a rapid cure of the composition is required. The curing rate may be a matter of seconds and be accompanied by evolution of heat which is not suitable for a composition for use as an orthopaedic bandage. Those compositions do not disclose mixtures with viscosity increasing agent. No medical uses for those curable compositions is disclosed or suggested.

Accordingly, the present invention provides an orthopaedic splinting or casting material which comprises a substrate which carries a hardenable resin containing a multifunctional vinyl ether monomer, an agent which when mixed with the monomer increases the viscosity thereof and a catalyst capable of causing the resin to harden when exposed to actinic radiation.

Suitable vinyl ether compounds are those which are multifunctional that is have more than one vinyl group per molecule and preferably have two vinyl groups per molecule. These compounds may be obtained by the reaction of alkylene polyols such as diols or triols with 2-chloroethylvinylether in the presence of sodium or potassium hydroxide and a tetralkyl ammonium salt phase transfer catalyst. Suitable vinyl ethers include diethylene glycol divinyl ether, trimethylol propane trivinyl ether. Difunctional vinyl ether monomers are preferred.

Suitably the multifunctional vinyl ether can form not less than 40% by weight of the resin and preferably not less than 45%. Suitably the multifunctional vinyl ether can form not more than 60% by weight of the resin and preferably not more than 55%.

Suitable multifunctional vinyl ether compounds will harden in the presence of a suitable catalyst on exposure to actinic radiation and, if desired, followed by exposure to heat. Suitable actinic radiation includes visible light and ultraviolet light. A suitable ultraviolet radiation has a wave length of from 240 to 400 nm and preferably 300 to 400 nm. The splinting or casting material may be exposed to the ultraviolet radiation for a period of from 5 to 10 minutes for example 7 minutes, 8 minutes in order to cause the resin to harden.

An agent is mixed with the multifunctional vinyl ether to increase its viscosity. Aptly this agent is a polymer.

Suitable polymers for mixing with the vinyl monomer may be those which are soluble in the monomer. Suitable polymers may have a high Tg that is above 75° C. Suitable polymers have the advantage that when the resin is hardened they reinforce the splint or cast so formed. A preferred polymer is polystyrene which has a Tg of around 90° C. Suitably the polymer can form not less than 40% by weight of the resin and preferably not less than 45%. Suitably the polymer can form not more than 60% by weight of the resin and preferably not more than 55%. Most preferably the polymer comprises 50% by weight of the resin.

Aptly the vinyl ether compound is a liquid at room temperature or at least at the temperature at which it is applied to the substrate. However, the liquid vinyl ethers are not sufficiently viscous not to flow from substrate once applied thereto. The vinyl ether can therefore be mixed with a polymer which is soluble in the monomer in the amounts described above to give a hardenable resin mixture of a suitable viscosity. The hardenable resin may be tacky when coated onto the substrate so that successive turns of the bandage laminate to each other when wrapped around a limb.

Suitable catalysts are described in for example United Kingdom Patent Nos. 1491540, 1518141 and 1516511 the disclosures of which are incorporated herein by reference.

The catalysts which are suitable for hardening the resin in the presence of ultraviolet radiation include the onium salts of group Vb, VIb, VIIb, VIII and Ib elements especially salts of positively charged sulphur or iodine. Thus favoured catalysts are diaryl iodonium and triarylsulphonium salts in which suitable anions include tetrafluoroborate, hexfluorophosphate, hexfluoroarsenate, hexfluoroantimonate, and perchlorate.

The catalysts which are suitable for hardening the vinyl ether monomer in the presence of visible light include mixed ligand arene cyclopentadienyl metal salts for example ($\eta^6$-pyrene) ($\eta^6$-cyclopentadienyl) $Fe^{II}$ hexafluorophosphate.

Optionally the catalyst may also contain a photosensitizer to extend the spectral response of the catalyst. Suitable photosensitizers include polyaryl compounds such as anthracene and pyrene; aryl ketones such as benzophenone and acetophenone; and acridine dyes.

Suitably the catalyst can be present as 0.01 to 1.0% by weight of the vinyl ether compound. When present a photosensitizer may be present in an amount upto 1% by weight of the catalyst.

Apt substrates in the form of flexible and/or extensible fabrics for carrying the hardenable resin and the catalyst include those described in United Kingdom No. 2092606B, U.S. Pat. No. 4427003 and European Patent No. 94222. Preferred fabrics are glass fibre fabrics which include those described in U.S. Pat. Nos. 3,421,501, 3,773,688, 3,787,272, 3,881,473, 3,882,857, 4,323,061, 4,502,479, 4,609,578 and 4,668,563. Other favoured substrates include those described in European Patent Application No. 290207, United Kingdom Patent Application No. 2214199 and International Patent Application No. 88/07847.

Thus the substrate may be any suitable substrate but knitted polymer or glass substrates are favoured of which glass substrates are preferred, for example a substrate such as in commercially available products such as Scotchcast or Dynacast. Other suitable substrates include woven and non-woven substrates, for example foams, apertured non-wovens and the like. When coated with the hardenable resin the substrate will be sufficiently porous so that the applied radiation can penetrate the turns of the fabric. Also when the resin has hardened then air may circulate to and moisture be removed from the skin beneath the splint or cast.

Suitably the hardenable resin and catalyst can comprise from 40 to 65% by weight of the orthopaedic splinting material for example 50%.

The splinting or casting material is preferably a bandage but other forms of sheet materials, for example those used to form slab casts, are also envisaged. In a slab cast the splinting material may be placed in a transparent bag for application to a limb.

The components of the hardenable resin and the catalyst may be mixed together and then applied to the substrate in the normal way. The coated substrate in bandage form can be rolled and sealed into a lightproof, waterproof pouch. In use the bandage is removed from the pouch and wrapped around the affected limb. The bandage is then exposed to ultraviolet radiation for 20 minutes.

If desired a separate layer may be interposed between the skin and the orthopaedic material. Suitable materials include foams, woven stockinette and other conventional types of padding.

In another aspect therefore the present invention provides an orthopaedic splinting or casting material which comprises a substrate which carries a hardenable resin containing a multifunctional vinyl ether monomer, an agent which when mixed with the monomer increases the viscosity thereof and a catalyst capable of causing the resin to harden when exposed to actinic radiation in which the orthopaedic splinting material is packed in a light proof package.

EXAMPLE 1

A mixture having the following composition was prepared by mixing together the components in the proportions shown:

| | |
|---|---|
| Diethyleneglycol divinyl ether | 50% by weight |
| Polystyrene | 50% by weight |
| *Catalyst | 1% by weight |

*The catalyst was diphenyl iodonium hexafluorophosphate.

The mixture was spread on a glass fibre substrate 8 cm wide at a weight per unit area of 140 gsm.

The bandage strip may be wound onto a core to form a roll and packed and sealed in a moisture-proof and light-proof polyethylene pouch.

A bandage may be made into a cast by removing the bandage from the pouch, wrapping the bandage round the limb, exposing the bandage to ultraviolet light at 300 nm for 7 minutes. A hard, non-tacky cast is formed.

EXAMPLE 2

A mixture having the following composition was prepared by mixing together the components in the proportions shown:

| | |
|---|---|
| Diethylene glycol divinyl ether | 50% by weight |
| Polystyrene | 50% by weight |
| *Catalyst | 1% by weight |
| Acridine Yellow G | 0.001% by weight |

*The catalyst was diphenyl iodonium hexafluorophosphate.

The mixture was spread on a glass fibre substrate 8 cm wide at a weight per unit area of 140 gsm.

The bandage strip may be wound onto a core to form a roll and packed and sealed in a moisture-proof and light-proof polyethylene-aluminium foil laminate pouch.

A bandage may be made into a cast by removing the bandage from the pouch, wrapping the bandage round the limb and exposing the bandage to visible light from a 500 watt quartz halogen lamp held about 15 cm from the surface of the bandage for about 5 minutes. A hard, non-tacky cast is formed.

I claim:

1. An orthopaedic splinting or casting material which comprises a substrate which carries a hardenable resin containing a multi-functional vinyl ether monomer, an inert agent which when mixed with the monomer increases the viscosity thereof and a catalyst capable of causing the resin to harden when exposed to actinic radiation.

2. A material according to claim 1 wherein the multi-functional vinyl ether monomer is a difunctional vinyl ether monomer.

3. A material according to claim 1 wherein said inert agent is soluble in the multi-functional vinyl ether monomer.

4. A material according to claim 1 wherein said inert agent comprises polystyrene.

5. A material according to claim 1 wherein the substrate comprises a flexible fabric.

6. A material according to claim 1 containing a photo-sensitizer to extend the spectial response of the catalyst.

7. A material according to claim 1 wherein the multi-functional vinyl ether monomer is present in an amount of from about 40% to about 60% by weight of the hardenable resin.

8. A material according to claim 1 wherein the hardenable resin comprises from about 40% to about 60% by weight of the material.

9. A splint or a cast comprising a material according to claim 1 which has been hardened under the influence of actinic radiation.

10. A method of forming a splint or a cast comprising placing the material according to claim 1 proximal to a limb and exposing the material to actinic radiation until a hardened splint or cast has been produced.

11. A light-proof sealed package containing a material according to claim 1.

12. A water-proof sealed package containing a material according to claim 1.

13. A material according to claim 1 wherein the substrate comprises an extensible fabric.

14. A material according to claim 1 wherein said inert agent is present in an amount of from about 40% to about 60% by weight of the hardenable resin.

15. A material according to claim 1 wherein said inert agent comprises a polymer.

16. A material according to claim 15 wherein said polymer has a Tg that is above 75° C.

* * * * *